(12) United States Patent
Siess et al.

(10) Patent No.: US 12,343,519 B2
(45) Date of Patent: Jul. 1, 2025

(54) PUMP INCLUDING A COMPRESSIBLE ROTOR HAVING OFFSET ROTOR BLADES

(71) Applicant: Abiomed Europe GmbH, Aachen (DE)

(72) Inventors: Thorsten Siess, Aachen (DE); Gerd Bruno Spanier, Aachen (DE); Tino Andreas Boelke, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 502 days.

(21) Appl. No.: 17/691,635

(22) Filed: Mar. 10, 2022

(65) Prior Publication Data
US 2022/0288381 A1    Sep. 15, 2022

Related U.S. Application Data

(60) Provisional application No. 63/159,665, filed on Mar. 11, 2021.

(51) Int. Cl.
| | | |
|---|---|---|
| *A61M 60/00* | (2021.01) | |
| *A61M 60/13* | (2021.01) | |
| *A61M 60/174* | (2021.01) | |
| *A61M 60/216* | (2021.01) | |
| *A61M 60/414* | (2021.01) | |
| *A61M 60/808* | (2021.01) | |
| *A61M 60/81* | (2021.01) | |

(Continued)

(52) U.S. Cl.
CPC .......... *A61M 60/808* (2021.01); *A61M 60/13* (2021.01); *A61M 60/174* (2021.01); *A61M 60/216* (2021.01); *A61M 60/414* (2021.01); *A61M 60/81* (2021.01); *F04D 19/00* (2013.01); *F04D 29/043* (2013.01); *F04D 29/18* (2013.01); *F04D 29/528* (2013.01)

(58) Field of Classification Search
None
See application file for complete search history.

(56) References Cited

U.S. PATENT DOCUMENTS

| 4,919,647 A | 4/1990 | Nash |
|---|---|---|
| 8,439,859 B2 | 5/2013 | Pfeffer et al. |

(Continued)

FOREIGN PATENT DOCUMENTS

EP    3088017 A1    11/2016

OTHER PUBLICATIONS

International Search Report and Written Opinion for International Application No. PCT/EP2022/056244 dated Jun. 23, 2022 (12 pages).

*Primary Examiner* — Sana Sahand
(74) *Attorney, Agent, or Firm* — Botos Churchill IP Law LLP

(57) ABSTRACT

Aspects of the present technology relate to compressible and expandable pumps. In one aspect, a pump is provided including a pump housing that is expandable and compressible and a rotor that is expandable and compressible and disposed in the pump housing. The rotor includes at least one rotor blade, a hub, and an axis of rotation. At least a portion of the at least one rotor blade extends from the hub along a first axis that is offset a predetermined distance from a radial axis of the rotor that traverses the axis of rotation. The pump further includes a drive shaft having a proximal end and a distal end, wherein the hub of the rotor is mounted to the distal end of the drive shaft and the drive shaft is rotated to rotate the rotor.

24 Claims, 17 Drawing Sheets

(51) Int. Cl.
    *F04D 19/00*     (2006.01)
    *F04D 29/043*     (2006.01)
    *F04D 29/18*     (2006.01)
    *F04D 29/52*     (2006.01)

(56) References Cited

U.S. PATENT DOCUMENTS

| | | |
|---|---|---|
| 2012/0041254 A1 | 2/2012 | Scheckel |
| 2013/0177432 A1* | 7/2013 | Toellner ............... F01D 5/147 |
| | | 416/225 |
| 2016/0279311 A1* | 9/2016 | Cecere ............... A61M 60/82 |
| 2019/0344001 A1 | 11/2019 | Salahieh et al. |
| 2020/0139029 A1 | 5/2020 | Scheckel et al. |
| 2020/0289732 A1 | 9/2020 | Toellner et al. |

* cited by examiner

PUMP INCLUDING A COMPRESSIBLE ROTOR HAVING OFFSET ROTOR BLADES

CROSS REFERENCE TO RELATED APPLICATIONS

This application claims the priority of and benefit from U.S. Provisional Application No. 63/159,665, filed Mar. 11, 2021, which is incorporated by reference herein.

TECHNICAL FIELD

The present technology relates to a fluid pump, such as blood pump, including a rotor having at least one rotor blade extending from a hub, where at least a portion of the at least one rotor blade extends from the hub along an axis that is offset with respect to a radial axis of the rotor.

BACKGROUND

Fluid pumps, such as blood pumps, are used in the medical field in a wide range of applications and for a wide range of purposes. For example, blood pumps may be used invasively and may be introduced via a blood vessel into the body of a patient and may be operated within the patient. Such pumps may be used, for example, in a cardiac chamber, such as the left ventricle, to assist the heart. In this case, the blood pump may be inserted into a patient via a femoral artery, using a catheter, and through the patient's vasculature into the left ventricle of the patient's heart. From this position, the blood pump draws in blood and expels it again into the aorta. In this manner, the heart's function may be fully or at least partially off-loaded to the pump.

BRIEF SUMMARY

In one aspect of the present technology, a pump, such as a blood pump insertable into a patient is provided. The pump may have a pump housing that is expandable and compressible and a rotor that is expandable and compressible and disposed in the pump housing. The rotor may have at least one rotor blade, a hub, and an axis of rotation. At least a portion of the at least one rotor blade may extend from the hub along a first axis that does not traverse the axis of rotation and is approximately orthogonal to the axis of rotation. The first axis is offset a predetermined distance from a radial axis of the rotor that passes through the hub and traverses the axis of rotation.

In some aspects, the hub is cylindrically shaped.

In some aspects, a first end of the hub is tapered with respect to a second end of the hub.

Although the rotor may be formed by any conventional technique, in any of the aspects described herein the rotor may be injection molded. The rotor also may be formed via vacuum molding, assure casting, and/or lost-molds. In any of the aspects described herein, the rotor may be injection molded from a single material.

In any of the aspects described herein, the rotor may have at least one second rotor blade that extends from the hub along a second axis that is also offset a predetermined distance from the radial axis of the rotor, which traverses the axis of rotation. In this aspect, the first axis and second axis are offset to opposite sides of the radial axis.

In any of the aspects described herein, at least one rotor blade may be helically wound around the hub. In some aspects, the at least one rotor blade may include a constant helical pitch. Alternately, in some aspects, the at least one rotor blade may include a varied pitch along a length of the hub.

In any of the aspects described herein, the first axis may be substantially parallel to the radial axis.

Regarding the shape of the rotor blades, in any of the aspects described herein, the at least one rotor blade may include a concave side and a convex side. In some aspects, when the rotor is compressed to a compressed state, the concave side of the at least one rotor blade may be laid against an exterior of the hub. In some aspects, the first axis may be offset from the radial axis in a direction of the convex side of the at least one rotor blade. In some aspects, at the at least a portion of the at least one rotor blade, the convex side may extend substantially tangentially from the hub. Alternately, in some aspects, at the at least a portion of the at least one rotor blade, the concave side may be offset from the radial axis in the direction of the convex side of the at least one rotor blade.

In any of the aspects described herein, the pump may have a drive shaft including a proximal end and a distal end. The hub of the rotor may be mounted to the distal end of the drive shaft and the rotation of the drive shaft rotates the rotor. In some aspects, the pump also may have a motor coupled to the proximal end of the drive shaft, where the motor is configured to rotate the drive shaft. In some aspects, the pump also may have a catheter assembled therewith. The catheter may have a distal end coupled to a proximal end of the pump housing. The drive shaft may be disposed through a hollow interior of the catheter. In any of the aspects described herein, the pump may be a blood pump and the pump housing may include an inlet and an outlet and rotation of the rotor may convey blood from the inlet to the outlet. In some aspects, such blood pumps may be insertable into a heart of a patient. For example, in some aspects, the blood pump housing may be insertable into a left ventricle of the heart of a patient.

In another aspect of the present technology, a rotor for a pump is provided. In any of the aspects described herein, the rotor may have at least one rotor blade, a hub, and an axis of rotation. At least a portion of the at least one rotor blade may extend from the hub along a first axis that is offset a predetermined distance from a radial axis of the rotor that traverses the axis of rotation of the rotor. In any of the aspects described herein, the at least one rotor blade of the rotor may be expandable and compressible relative to the hub.

DETAILED DESCRIPTION

Figure 1:
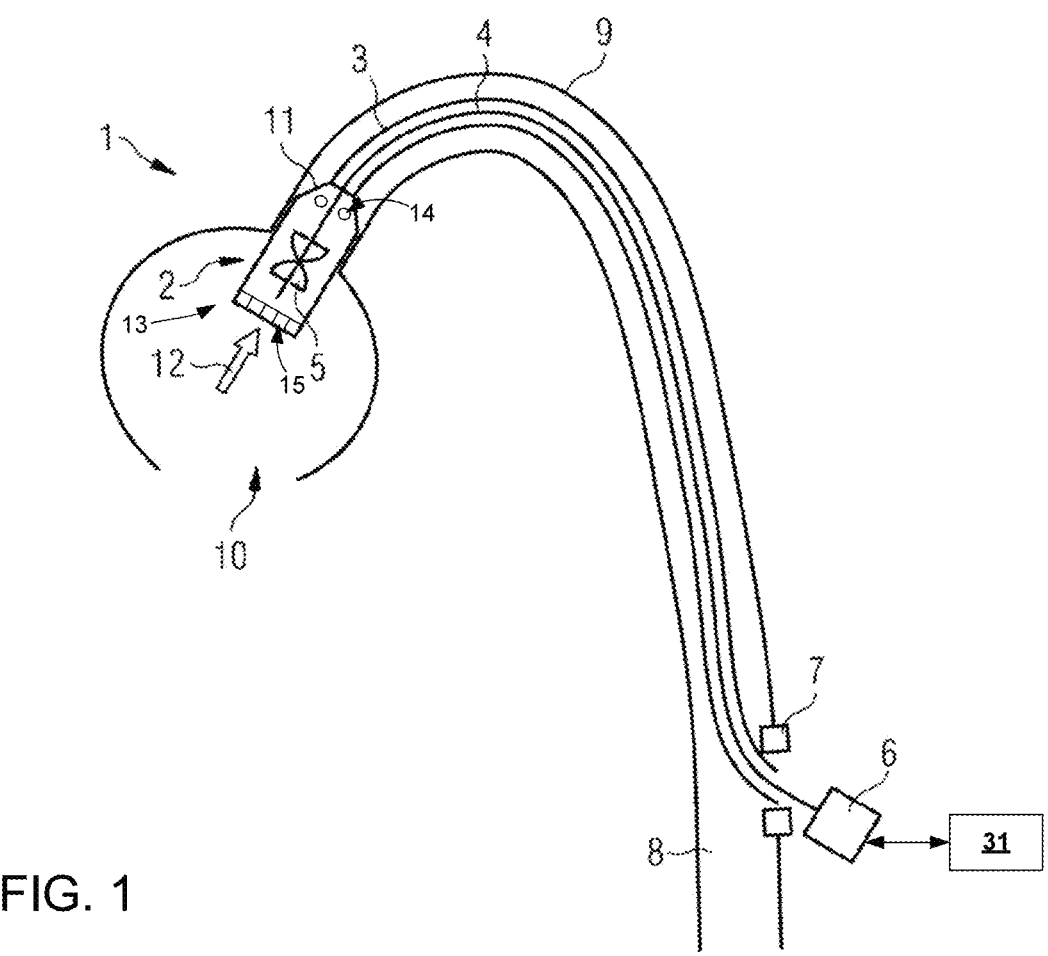
FIG. 1 illustrates a pump system in accordance with the present technology.

Aspects of the present technology are described in detail with reference to the drawing figures wherein like reference numerals identify similar or identical elements. It is to be understood that the disclosed aspects are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As is known, intravascular blood pumps may be introduced via a blood vessel into the body of a patient and may be operated within the patient to support the heart. Such pumps may be used, for example, in a cardiac chamber, such as the left ventricle, to assist the heart. Such blood pumps may have a rotatable rotor including rotor blades. The rotation of the rotor blades causes the blood to flow within the patient in the same manner as the patient's heart. To enable the pump to be transported and deployed within the patient, the dimensions of the blood pump may be suitably small. However, the small dimensions may reduce the efficiency of the pump. For example, a smaller rotor may not pump blood as efficiently as a larger rotor. In contrast, a large rotor may not be easily insertable into the patient. This problem may be alleviated by constructing a pump with a compressible rotor for more efficient deployment into the patient and expandable to pump blood more efficiently. However, this solution may present other problems. For example, when the rotor is compressed, the rotor blades may be subjected to stresses and strains and may be deformed when subjected to compression forces. In this regard, the rotor blades may need to be deformed a great deal in locally bounded regions for folding onto a hub of the rotor to achieve a compressed state. Under such forces, the shape of the rotor after subsequent expansion may be altered from its original uncompressed shape and the subsequent uncompressed shape and performance may thus be unpredictable or otherwise compromised. Moreover, it is challenging to select materials that have suitable tolerances and properties that allow the rotor to withstand the compression forces to which it is subjected while still allowing the rotor to be compressible. Consequently, the manufacture of such expandable and compressible rotors remains challenging.

Accordingly, the inventors have recognized that a need exists for rotor configurations that both (i) permit rotors to be more easily compressed and reliably withstand the compression forces, stresses, and strains to which the rotor is subjected when compressed; and (ii) provide for easy and cost-effective manufacture of such rotors.

Turning to the figures, FIG. 1 shows a schematic overview of a pump in accordance with the present technology. The pump 1 may include a pump housing 2 and a catheter 3 having a lumen therethrough. Pump housing 2 may include proximal end 11 and distal end 13. In some embodiments, the distal end 13 may include one or more openings 15 forming an inlet for drawing blood into pump housing 2. In one aspect, openings 15 may form an inflow cage. The direction of the inflowing blood is symbolized by arrow 12. Proximal end 11 may include one or more openings 14 forming an outlet for conveying the blood drawn in by the inlet into a blood vessel of a patient.

A drive shaft 4 may be arranged in the lumen of catheter 3. The proximal end of drive shaft 4 may be attached to a motor 6 and a distal portion of the drive shaft may extend into the interior of pump housing 2. A rotor 5 may be mounted to the distal portion of drive shaft 4 and arranged in pump housing 2. Motor 6 may rotate the drive shaft 4, which may rotate rotor 5. It is to be appreciated that drive shaft 4 may be flexible to enable deployment of drive shaft 4 and catheter 3 into the patient.

As illustrated in FIG. 1, the pump 1 may be introduced into a blood vessel of a patient via a port 7. For example, pump 1 may be introduced and provided through an arteriotomy in femoral artery 8 and passed through aortic arch 9 and into a heart ventricle 10 of the patient, such that pump housing 2 lies in the region of the aortic valve (not shown). It is to be appreciated that distal end 13 of pump housing 2 may extend into a left ventricle of the patient and proximal end 11 is disposed in the aorta of the patient. Rotor 5 may be rotated by drive shaft 4 and motor 6 at a speed between 3,000 and 50,000 rpm (revolutions per minute) for conveying blood from heart ventricle 10 into the openings 15 of the inlet at distal end 13 of pump housing (as indicated by arrow 12) and out of the openings 14 of the outlet at proximal end 11 into the aorta.

In one aspect, pump 1 may include a controller 31 for controlling and driving motor 6 to control the operation of pump 1. The controller may be integrated in motor 6 or be separately located from motor 6.

In one aspect, pump housing 2 and rotor 5 may be configured to be radially compressible to a compressed state to enable efficient deployment of pump 1 through the blood vessel of the patient. Moreover, after the placement of pump housing 2 and rotor 5 in and/or proximately to the ventricle 10 of the patient, pump housing 2 and rotor 5 may be configured to be radially expandable to an expanded state for normal operation.

Figure 2A:
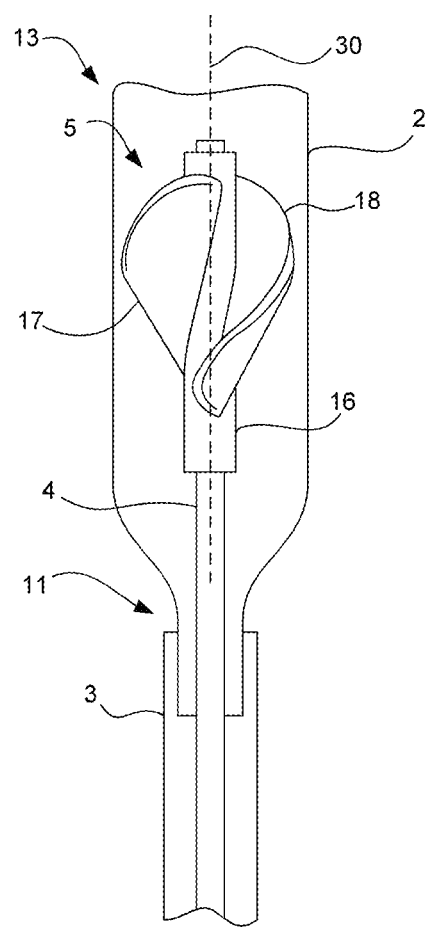
FIG. 2A is a partial side view of a distal portion of the pump of FIG. 1 in accordance with the present technology.

For example, FIG. 2A shows the interior of pump housing 2 and a distal portion of catheter 3. As shown in this view, rotor 5 may be mounted to a distal portion of drive shaft 4 and disposed within the interior of pump housing 2.

Referring to FIGS. 4A-4D, rotor 5 is shown in greater detail in accordance with an aspect of the present technology. It is to be appreciated that rotor 5 is shown in an uncompressed or expanded state; i.e., at rest, and free of externally applied forces (e.g., free of compression forces in the compressed state or pressures and rotational forces during operation in the expanded state). Rotor 5 includes radially compressible rotor blades 17, 18 and hub 16. Blades 17, 18 may extend radially from the exterior of hub 16. Hub 16 extends from a proximal end 20 to a distal end 19 of rotor 5 and is coaxially aligned with a rotational axis 30 of rotor 5. A central bore or channel 29 (shown in FIG. 4C) may extend through hub 16 from end 20 to end 19. A distal portion of a drive shaft of a pump, such as drive shaft 4 of pump 1, may extend through the central bore 29 to mount and rotate rotor 5 within a pump housing, such as pump housing 2, of a pump.

In one aspect, rotor blades 17, 18 may have a curved design in the radial direction and a curved enlacement in the axial direction. Each blade 17, 18 may include a first side having a convex surface (e.g., a suction side) and a second side having a concave surface (e.g., a pressure side). For example, blade 17 includes convex side 21 and concave side 22 and blade 18 includes concave side 23 and convex side 24. Blades 17, 18 may be made of flexible material(s) that enable blades 17, 18 to fold onto hub 16 when compressed to a compressed state. The radially curved design of rotor 5 defines a desired or predetermined compression or crimping direction of the rotor blades 17, 18 (i.e., the direction of the concave side of each blade 22) when blades 17, 18 are compressed to a compressed state. In such embodiments, a stretch may occur at the convex side of the blade 21.

Referring again to FIG. 2A, hub 16 of rotor 5 and housing 2 are each coaxially aligned with the axis of rotation 30 of rotor 5. Pump housing 2 and rotor 5 are shown in FIG. 2A in an uncompressed or expanded state at rest and not subject to external forces. Pump housing 2 and rotor 5 may be radially compressed to a compressed state. In the compressed state, pump housing 2 may be deployed into the patient using a delivery system. For example, in one aspect, the delivery system may include an introducer sheath that constrains pump housing 2 and rotor 5 to maintain pump housing 2 and rotor 5 in the compressed state. While constrained in the introducer sheath, the pump housing 2 and rotor 5 are inserted into the body of the patient to a desired position. Pump housing 2 may then be advanced distally, e.g., by pushing catheter 3, such that pump housing 2 exits a distal end of the introducer sheath.

Once in a desired position within the patient, pump housing 2 and rotor 5 are radially expanded to an expanded state. In such embodiments, this expansion position may be defined by an end of the catheter. For example, the rotor may unfold by releasing the pump out of the delivery system (e.g., an introducer sheath). In one aspect, pump housing 2 may be made of a shape-memory material that returns pump housing 2 to the expanded state when pump housing 2 is not acted on by external compression forces. In another aspect, pump 1 may include an actuation means for expanding pump housing 1 to an expanded state. Thereafter, rotor 5 may be rotated by drive shaft 4 to radially unfold rotor blades 17, 18 to an expanded state. In one aspect, rotor 5 may be made of material that returns rotor 5 to the expanded state without requiring the rotation of rotor 5.

Figure 2B:
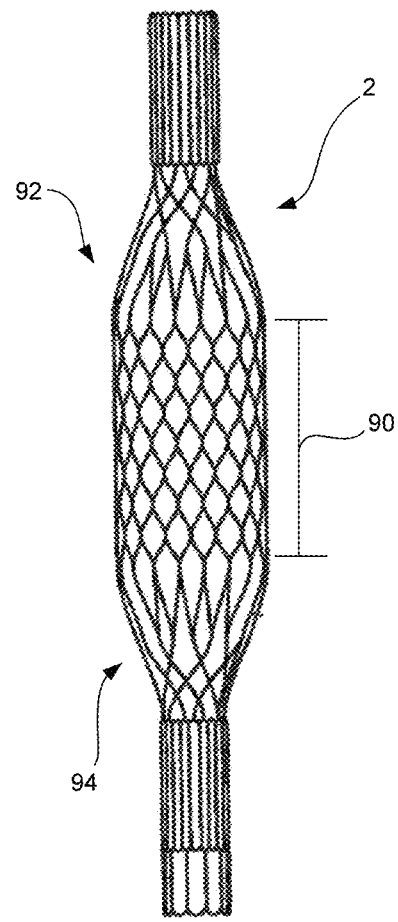
FIG. 2B is an exemplary pump housing structure for use with the pump of FIG. 1 in accordance with the present technology.

Referring to FIG. 2B, in one aspect, pump housing 2 may comprise a radially expandable and compressible structure made of a wire mesh or a mesh of fibers. Alternatively, pump housing 2 may comprise a plurality of helical struts that forms a radially expandable and compressible structure. In either case, a hose or sealing structure (e.g., a polymer film) may be disposed over portion 90 (or at least a part of portion 90) of pump housing 2 to prevent the ingress or egress of blood into portion 90. In such embodiments, the film may create a pump chamber with hydraulic performance (e.g., for pumping). The hose may be made of a polyurethane and be generally cylindrically shaped. With the hose sealing portion 90, distal portion 92 of pump housing 2 and proximal portion 94 remain unsealed. In this way, the apertures between the wire or fibers forming the structure of housing 2 at distal portion 92 may form the inlet of pump housing 2 and the apertures at distal portion 94 may form the outlet of pump housing 2. In alternative aspects, the hose or sealing structure may cover and seal the entirety or at least a majority of the pump housing 2 and the hose or sealing structure may include apertures at the proximal and distal ends of the sealing structure to form an inlet and outlet for pump housing 2.

Exemplary radially expandable and compressible pump housings, structures for expanding and compressing such pump housings, and methods for implementing such pump housings for use with a pump such as pump 1 are described in U.S. patent application Ser. No. 16/658,256, U.S. Pat. No. 8,439,859, and U.S. Patent Application Publication No. 2020/0289732 A1, the entire contents of which are hereby incorporated by reference herein.

Figure 3A:
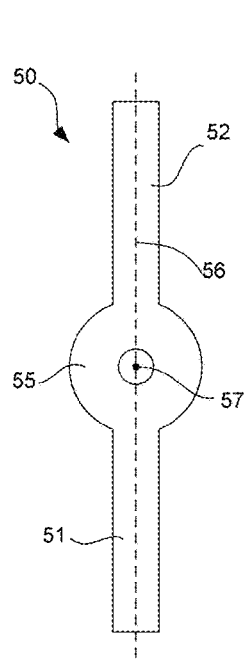
FIG. 3A illustrates a prior art rotor configuration.

Rotor blades, such as rotor blades 17, 18 of rotor 5, may extend from a hub, such as hub 16, along a radial axis that traverses the axis of rotation 30 of the rotor through the center of the hub. This is illustrated in the rotor configuration 50 of FIG. 3A, where the blades 51, 52 extend from hub 55 along a radial axis 56 that traverses the axis of rotation 57 of rotor 5 through the center of hub 55. The blades, 51, 52 are illustrated as straight, but they may be curved.

In accordance with the present technology, rotor blades 17, 18 may be modified to extend from respective axes that are offset from the radial axis that traverses the axis of rotation. Each of these designs will first be described in relation to FIGS. 3B-3D in the context of the simple case of planar rotor blades extending from a hub, but, as described below, the designs are equally applicable to curved blades, such as blades 17, 18 of rotor 5 described above.

Figure 3B:
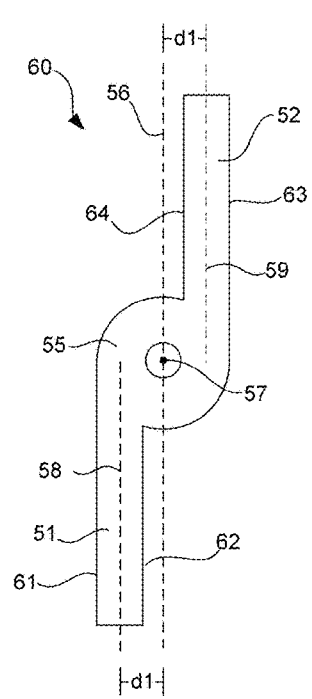
FIGS. 3B-3D illustrate various rotor configurations in accordance with the present technology.

For example, referring to FIG. 3B, a rotor configuration 60 in a resting and uncompressed state (i.e., under no external forces) is shown in accordance with the present technology. Rotor configuration 60 includes radially compressible and expandable rotor blades 51, 52 and a cylindrical hub 55. Blades 51, 52 extend from hub 55 along respective axes that are eccentric relative to the center of hub 55 or offset from radial axis 56. As shown in rotor configuration 60 of FIG. 3B, rotor blade 51 extends along axis 58 and rotor blade 52 extends along axis 59. Axes 58 and 59 are each offset a predetermined distance d1 from axis 56 and are parallel to axis 56. Rotor blade 51 includes sides 61 and 62, where side 61 is disposed further from axis 56 than side 62. Rotor blade 52 includes sides 63 and 64, where side 63 is disposed further from axis 56 than side 64. In the rotor configuration 60, the offset between axes 58, 59 and axis 56 is such that side 61 of blade 51 and side 63 of blade 52 each extend approximately tangentially relative to a circular cross-section of hub 55. It is to be appreciated that the degree of offset between axis 56 and axes 58, 59 may be less or more than d1, but greater than zero. For example, in rotor configuration 70, the offset between axis 56 and axes 58, 59 is a predetermined distance d2, which is a distance less than d1. As another example, in rotor configuration 80, the offset between axis 56 and axes 58, 59 is a predetermined distance d3, which is a distance greater than d1. In the rotor configuration 80, the offset between axes 58, 59 and axis 56 is such that side 62 of blade 51 and side 64 of blade 52 each extend approximately tangentially relative to a circular cross-section of hub 55. As will be described in greater detail below, rotor configurations, such as configurations 60, 70, 80, where the rotor blades extend from the hub at an offset to a radial axis through the center of the hub, offer several advantages in the operation of the pump.

Figure 3C:
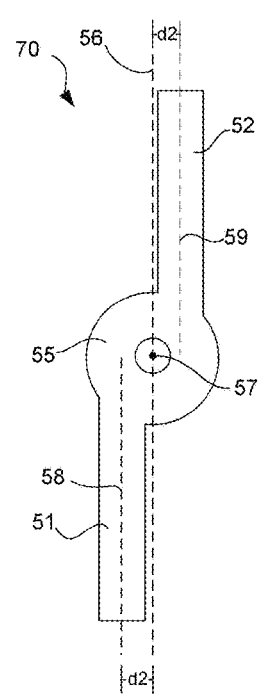
Figure 3D:
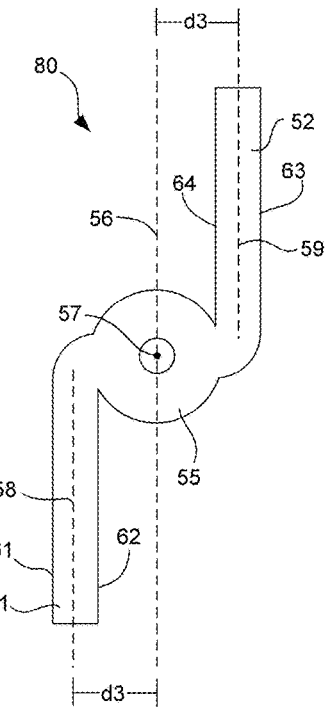

Although the offsets described above with respect to axis 56 and axes 58, 59 in configurations 60, 70, 80 are described using rotor blades 51, 52, which are shown in FIGS. 3B-3D extending linearly from a rotor hub 55, the design aspects of configurations 60, 70, 80 relating to the offset (or lack thereof) described above may also be described in the context of rotor blades that wrap helically around a hub, such as rotor blades 17, 18 of rotor 5 described above.

Figure 4A:
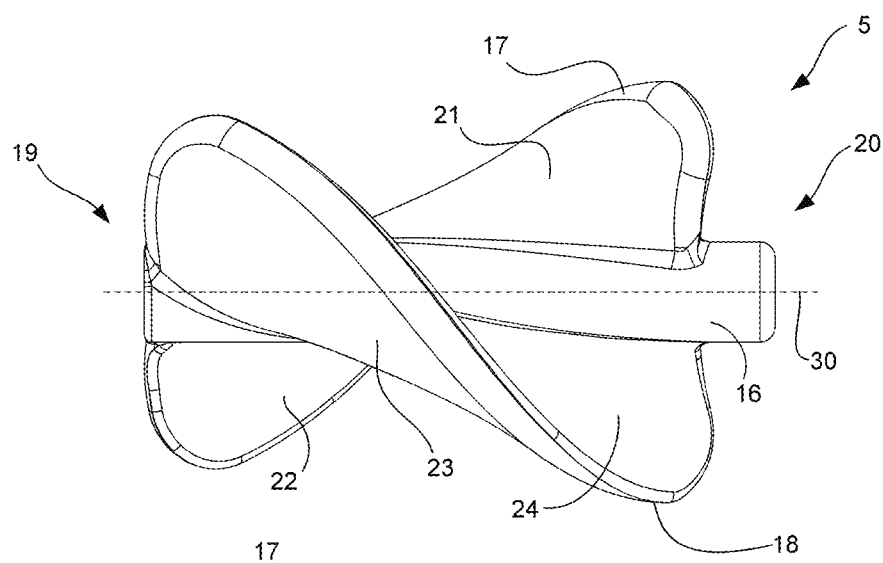
FIGS. 4A-4D include various views of a compressible and expandable rotor in an uncompressed or expanded state and at rest in accordance with the present technology.
Figure 4B:
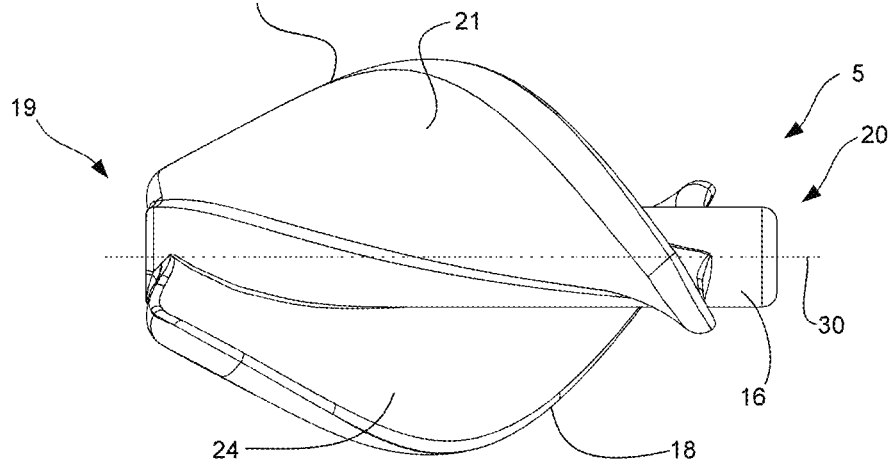
Figure 4C:
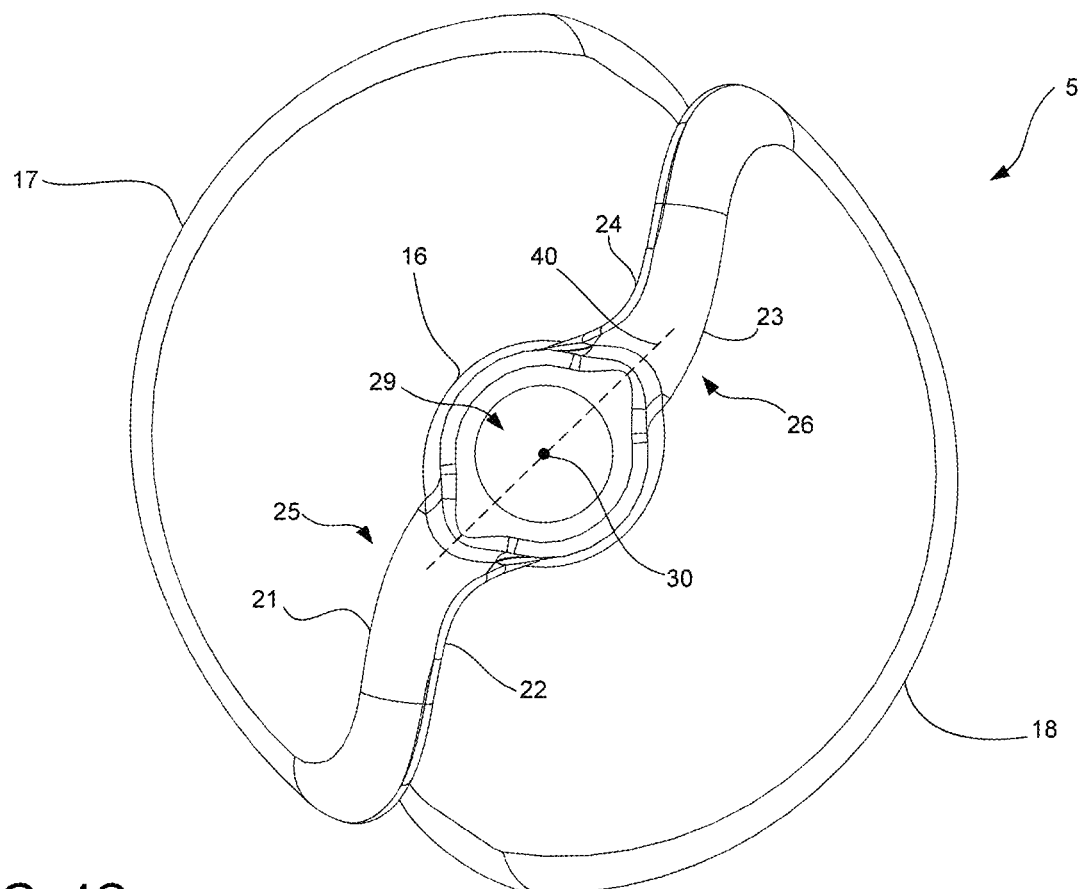
Figure 4D:
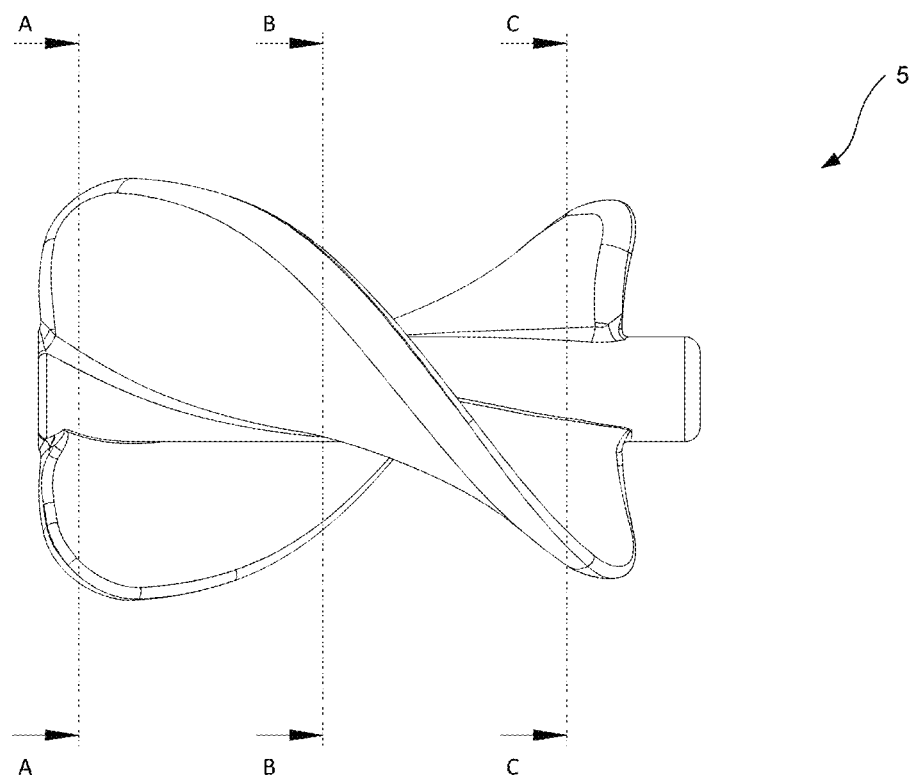
Figure 4E:
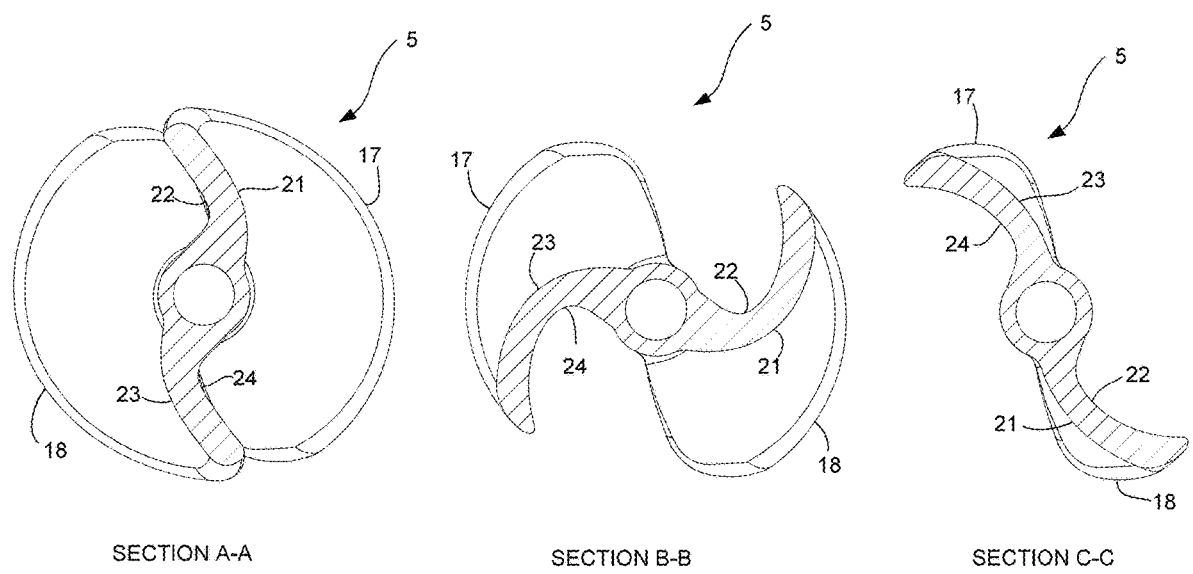
FIG. 4E includes cross-sectional views of the compressible and expandable rotor of FIGS. 4A-4D along sections A-A, B-B, and C-C shown in FIG. 4D in accordance with the present technology.

The transverse or offset of the blades relative to the hub may be achieved at the point of attachment of the blades to the hub relative to the axis that passes orthogonally to the axis of rotation of the hub, or the curvature of the blades as they extend beyond the hub. With respect to the extension of rotor blades 17, 18 from hub 16, rotor 5 is designed in a similar manner to configuration 50 described above. As best seen in FIG. 4C, where distal end 19 of rotor 5 is shown, blades 17, 18 include portions 25, 26. Portion 25 is a portion of blade 17 disposed proximately to hub 16 and portion 26 is a portion of blade 18 that is disposed proximately to hub 16. In one aspect, portions 25 and 26 are portions of blades 17 and 18, respectively, that are disposed directly adjacent to hub 16. As shown in FIG. 4C, portions 25 and 26 extend along a radial axis 40 that orthogonally traverses the axis of rotation 30 of rotor 5 and extends through the center of hub 16. It is to be appreciated that, as seen in the cross-sectional views of rotor 5 (FIG. 4D) in FIG. 4E, portions 25 and 26 (FIG. 4C) extend from the hub as illustrated in FIG. 4C (i.e., along radial axis 40) along the length of the hub (i.e., from distal end 19 to proximal end 20 of hub 16). In this configuration, as illustrated in the FIG. 4E cross sections along A-A, B-B, and C-C of FIG. 4C, the curvature of the outer portions of blades 17, 18 varies depending on the position along the length of the hub 16 from which the blades 17, 18 extend. FIG. 4D, illustrates the three positions on the hub from which that correspond to the three cross-sections, A-A, B-B, and C-C. As illustrated in FIG. 4E, at cross-section A-A, the inner curvature of the concave sides 22, 24 of the blades, 17, 18 is tighter (i.e., at a smaller angle) than the curvature of the convex sides 21, 23 of the blades (which form a larger angle). This is even more readily observed in the B-B cross-section. However, in the C-C cross section, the convex degree of curvature of sides 21, 23 and concave degree of curvature of sides 22, 24 are roughly complementary. Therefore, in the aspect illustrated in FIGS. 4A-4E, the pitch of the each of the outer portions of the blades 17, 18 varies along the length of the hub 16.

In one aspect, rotor 5 may be modified such that, similar to the blade offsets described above with respect to configurations 60, 70, 80, at least a portion of each of blades 17 and 18, such as portions 25 and 26, extend from the hub 16 along a respective axis or axes that are offset relative to radial axis 40.

For example, referring to FIGS. 5A-5D, rotor 105 is shown in accordance with another aspect of the present technology. It is to be appreciated that rotor 105 is shown in an uncompressed or expanded state and at rest and free of externally applied forces (e.g., free of compression forces in the compressed state and pressures and rotational forces during operation in the expanded state). Rotor 105 includes radially compressible rotor blades 117, 118 and hub 116. Blades 117, 118 extend radially from the exterior of hub 116. Hub 116 extends from a proximal end 120 to a distal end 119 of rotor 105 and is coaxially aligned with a rotational axis 130 of rotor 105. A central bore or channel 129 (shown in FIG. 5C) extends through hub 116 from end 120 to end 119. A distal portion of a drive shaft of a pump, such as drive shaft 4 of pump 1, may extend through the central bore 129 to both support and rotate rotor 105 within a pump housing, such as pump housing 2, of a pump. As will be described in greater detail below, rotor 105 may be molded over the distal portion of drive shaft 5.

In one aspect, hub 116 is cylindrically shaped and includes a constant diameter from end 119 to end 120. However, as will be described below, in some aspects, the diameter of hub 116 may taper from one end to the other end.

In one aspect, rotor blades 117, 118 may have a curved design in the radial direction and a curved enlacement in the axial direction. Each blade 117, 118 may include a first side having a convex surface (e.g., a suction side) and a second side having a concave surface (e.g., a pressure side). For example, blade 117 may include convex side 121 and concave side 122 and blade 118 includes convex side 123 and concave side 124. Blades 117, 118 are attached to the hub 116 by flexible material(s) such that blades 117, 118 are foldable onto hub 116 when compressed to a compressed state. In the compressed state, concave surfaces 122, 124 lay closer to, or even against, the exterior of hub 116. Given the blade curvature, blades 117, 118 each may at least partially wrap around hub 116. The radially curved design of rotor 105 defines a preferred compression or crimping direction of the rotor blades 117, 118 (i.e., the direction of the concave side of each blade) when blades 117, 118 are compressed to a compressed state.

In one aspect, blades 117, 118 each include a constant helical pitch, however, as described below, in other aspects, blades 117, 118 may each include a variable pitch.

Figure 5A:
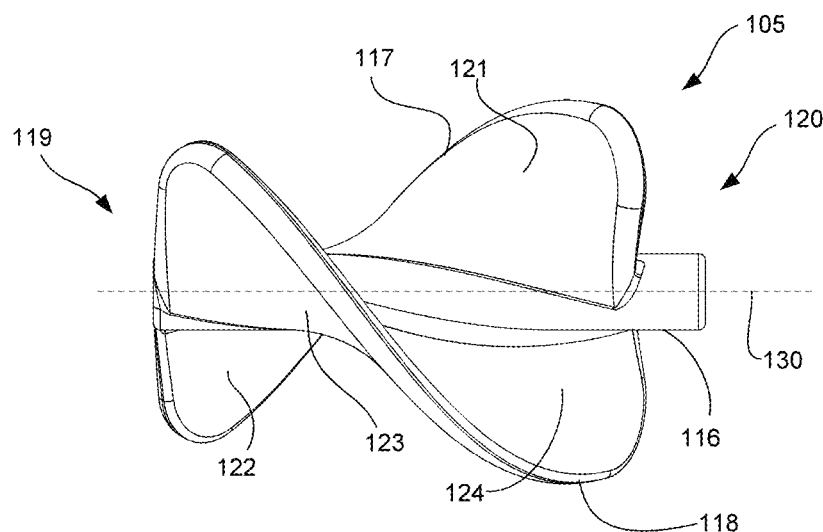
FIGS. 5A-5D include various views of include various views of another compressible and expandable rotor in an uncompressed or expanded state and at rest in accordance with the present technology.
Figure 5B:
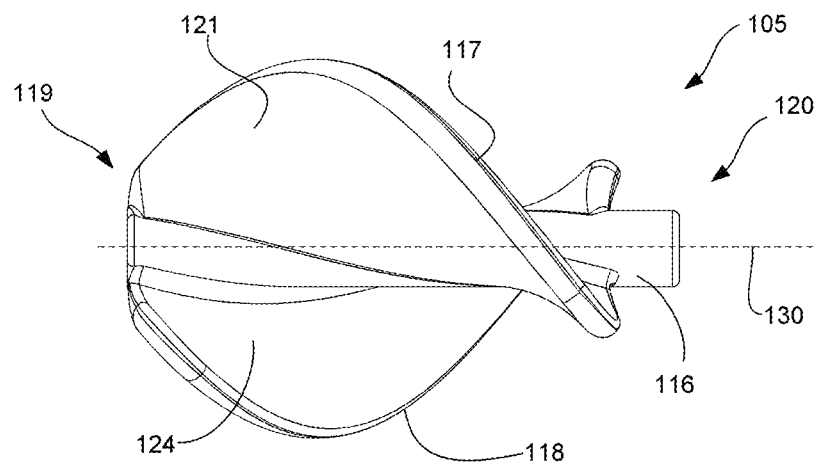
Figure 5C:
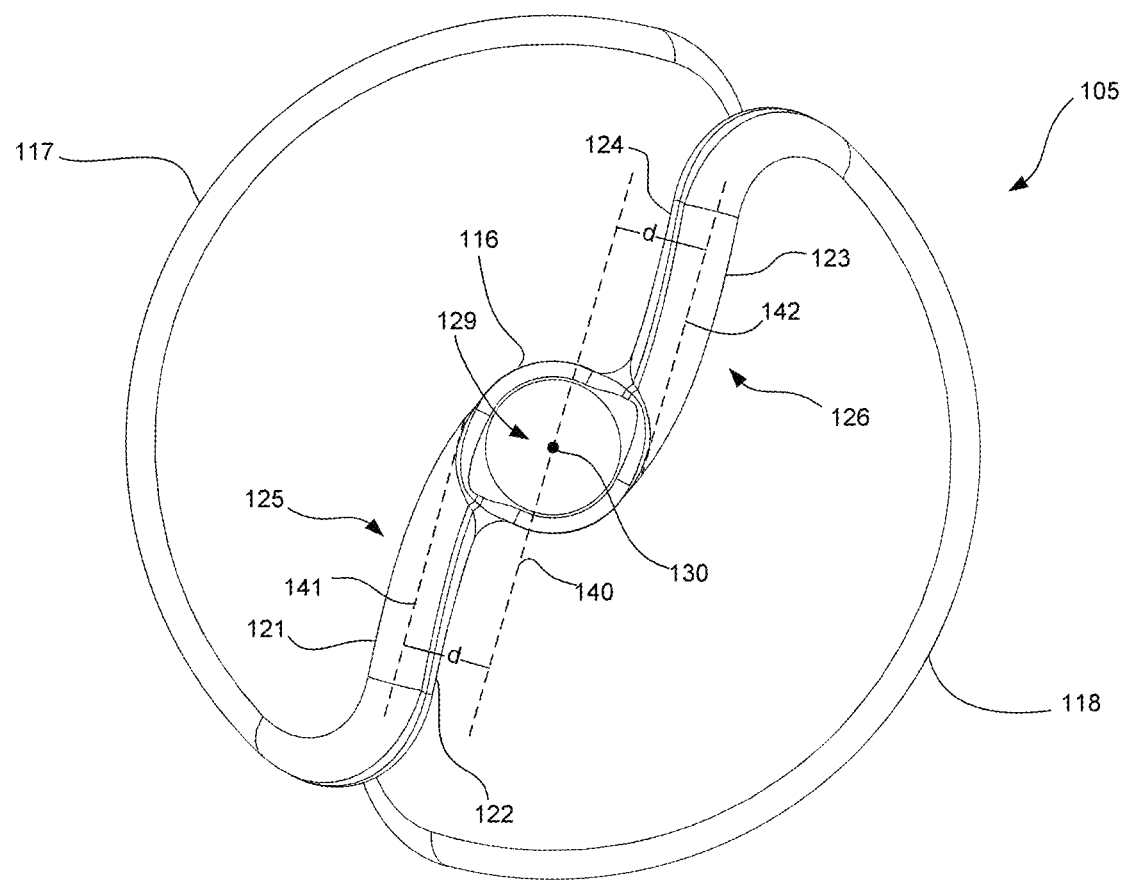
Figure 5D:
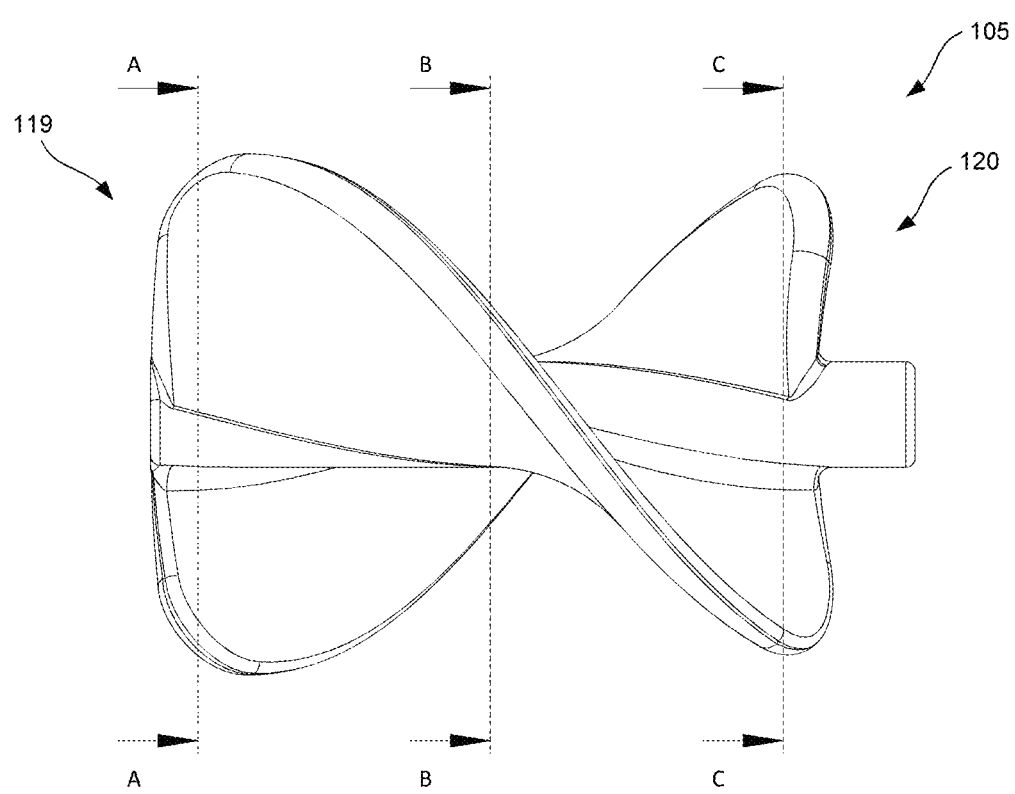

As best seen in FIG. 5C, where distal end 119 of rotor 105 is shown, blades 117, 118 may include inner portions 125, 126. Portion 125 is a portion of blade 117 that extends from hub 116 toward the outer edge of blade 117 and portion 126 is a portion of blade 118 that extends from hub 116 toward the outer edge of blade 118. In one aspect, portions 125 and 126 are portions of blades 117 and 118, respectively, that that are disposed directly adjacent to hub 116 and terminate before the respective edges of each of blades 117, 118. In another aspect, portions 125, 126 each extend the entire distance from hub 116 to the outer edges of blades 117, 118, respectively.

As shown in FIG. 5C, portion 125 extends along axis 141 and portion 126 extends along axis 142. Axes 141, 142 are eccentric with respect to the center of hub 116. Moreover, axes 141, 142 are each offset a predetermined distance d from radial axis 140 and are substantially parallel to radial axis 140. In this context of describing the relationship of axes 141, 142 with respect to radial axis 140, "substantially parallel" means that the predetermined distance d between each of axes 141, 142 and radial axis 140 is approximately (e.g., +/−20%) the same or constant throughout the length of each of portions 125, 126. In other words, even if each of axes 141, 142 tilt slightly (e.g., 1° to 20°) with respect to radial axis 140, axes 141, 142 may still be considered to be "substantially parallel" to radial axis 140 for the purposes of describing the present technology.

Radial axis 140 extends through and orthogonally traverses the axis of rotation 130. It is to be appreciated that, as seen in the cross-sectional views of rotor 105 in FIG. 5E (which are cross-sections of rotor 105 taken at different positions along hub 116), in one aspect, the offset of axes 141, 142 with respect to radial axis 140 persists from distal end 119 to proximal end 120 of hub 116. In other words, at any point axially along hub 116, portions 125, 126 may extend from hub 116 at a predetermined offset distance d from radial axis 140. As described below, in other aspects, the offset between axes 141, 142 relative to radial axis 140 may only be along some portion of the hub (e.g., for a proximal, distal, and/or central portion of rotor 105). Moreover, in some aspects, the predetermined distance d of the offset may vary at different locations along the axial length of rotor 105.

Referring again to FIG. 5C, in one aspect, portion 125 of blade 117 is offset from axis 140 in the direction of convex side 121 of blade 117 and portion 126 of blade 118 is offset from axis 140 in the direction of convex side 123 of blade 118. In this way, portions 125, 126 are entirely offset to opposite sides of axis 140. In one aspect, the predetermined distance d of the offset is selected such that the surface of convex side 121 of portion 125 extends substantially tangentially (i.e., substantially along a tangent line) extending from the outer circumference of hub 116 and the surface of convex side 123 of portion 126 extends substantially tangentially from the outer circumference of hub 116. Moreover, the predetermined distance d is selected such that, at portion 125, the concave side 122 is offset or spaced from axis 140 in the direction of convex side 121 and, at portion 126, the concave side 124 is offset or spaced from axis 140 in the direction of convex side 123. In other words, each of sides 121, 122, 123, 124 are eccentric with respect to the center of hub 116 as well as offset from axis 140.

As described above, the offset position of each of portions 125, 126 of rotor 105 may provide several advantages relative to rotors, such as, rotor 5 and rotor configuration 50 that do not include such an offset.

Figure 6A:
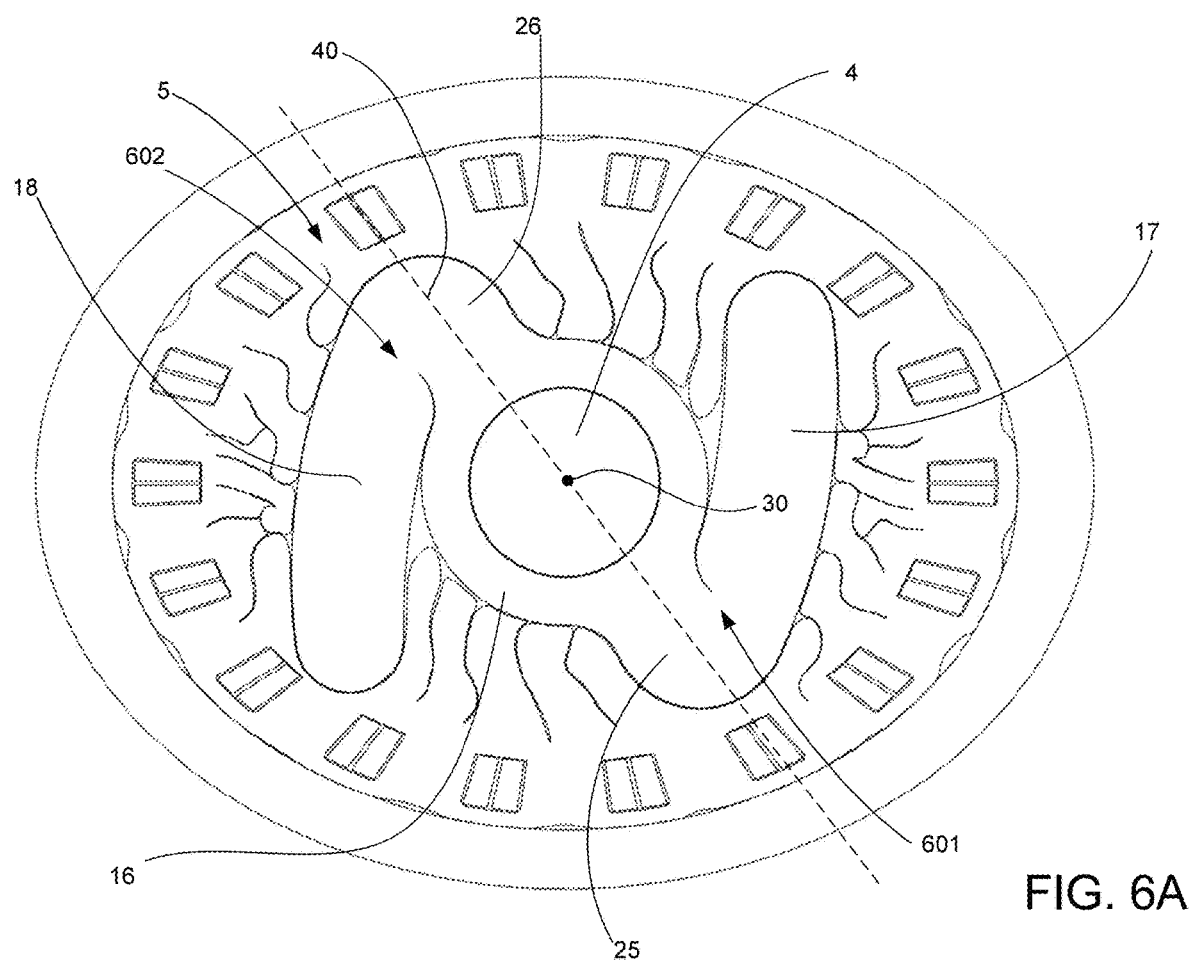
FIG. 6A is an illustration of the rotor of FIGS. 4A-4D in a compressed state in accordance with the present technology.
Figure 6B:
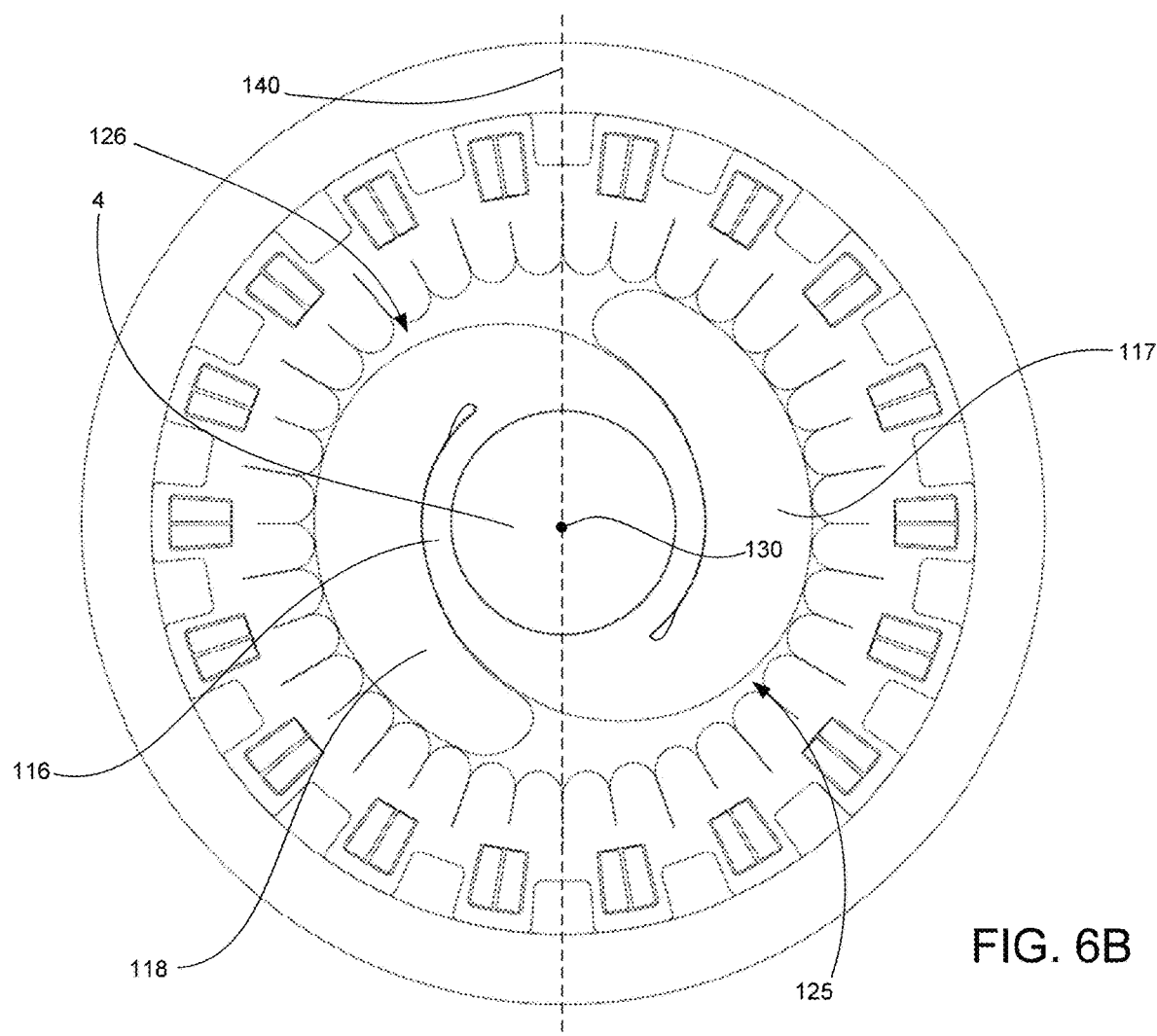
FIG. 6B is an illustration of the rotor of FIGS. 5A-5D in a compressed state in accordance with the present technology.

For example, referring to FIGS. 6A and 6B, FIG. 6A shows rotor 5 in a compressed state and FIG. 6B shows rotor 105 in a compressed state. As shown in FIG. 6A, in the compressed state, rotor blades 17, 18 are folded onto hub 16. However, the folding produces respective sharp kinks 601, 602 in blades 17, 18. Kinks 601, 602 may occur in rotor 5 because portions 25 and 26 of blades 17, 18 extend along radial axis 40 from hub 16 and thus the rotor blades 17, 18 are not prevented from buckling back on to hub 16. In this way, blades 17, 18 are more likely to yield or bend at sharp angles radially spaced from hub 16 and thus form kinks 601, 602. This kinking may put stress and strain on the rotor blades 17, 18 and the hub 16 and increases the likelihood that blades 17, 18 will be permanently deformed with respect to their original uncompressed, expanded state.

The offset design of rotor blades 117, 118 avoids the sharp kinking that occurs with the rotor blades 17, 18 of rotor 5. For example, as shown in FIG. 6B, in the compressed state, the offset of portions 125, 126 of rotor blades 117, 118 with respect to radial axis 140 allows blades 117, 118 to wrap at least partially around hub 116, conforming to the hub curvature. Consequently, the sharp kinking illustrated in FIG. 6A that rotor 5 experiences in the compressed state is absent in the compressed rotor illustrated in FIG. 6B. Due to the eccentric positions of portions 125, 126 with respect to hub 116, there is more space on the concave sides 122, 124 of each of blades 117, 118 such that blades 117, 118 may wrap around hub 116 more smoothly such that the concave sides 122, 124 lay more evenly against hub 116 in the compressed state to mitigate kinking in each of blades 117, 118. Since blades 117, 118 lay more evenly against hub 116, the forces on blades 117, 118 when compressed are transferred into a torque on the outer diameter of the hub 116, thereby reducing or eliminating kinking in blades 117, 118 when compressed. In this way, the offset position of blades 117, 118 reduces the stress on the blades 117, 118 in the compressed state and blade deformation that may result from such stress. The reduced stress on blades 117, 118 in the compressed state further allows blades 117, 118 to unfold to their natural position in the uncompressed, expanded state due to the reduced likelihood of permanent deformation of blades 117, 118 due to blade stress in the compressed state. Moreover, this also allows the shape of rotor 105 after decompression to be more consistent than that of rotor 5.

Mitigating the sharp kink of the blades 117, 118 in the compressed state may reduce and also mitigate the stress and strain on hub 116 in the region where the rotor blades 117, 118 attach to hub 116. This may allow the thickness and overall diameter of hub 116 to be reduced relative to hub 16 of rotor 5 because thicker hubs are not required to withstand the greater stresses.

Figure 7A:
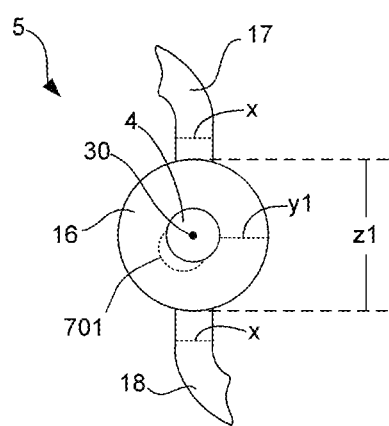
FIG. 7A is a partial view of the rotor of FIGS. 4A-4D in accordance with the present technology.

For example, referring to FIG. 7A, hub 16 of rotor 5 may have a diameter z1 and a thickness y1. Rotor blades 17, 18 each include a thickness x. Due to the stress on hub 16 when rotor 5 is compressed and/or during rotation of rotor 5, thickness y1 is selected to be sufficiently large to prevent delamination of an inner diameter of hub 16 from drive shaft 4 of pump 1. Delamination may occur where the pull stress is the highest on hub 16. An exemplary delamination of hub 16 is illustrated in FIG. 7A by reference number 701. It is to be appreciated that the thickness y1 of hub 16 is greater than the thickness x of each of rotor blades 17, 18.

Figure 7B:
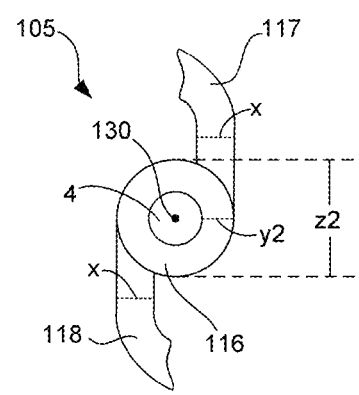
FIG. 7B is a partial view of the rotor of FIGS. 5A-5D is accordance with the present technology.

Referring to FIG. 7B, the design of rotor 105 may reduce the stress on hub 116. Thus, the thickness y2 of hub 116 is selected to be less than the thickness y1 of hub 16 without reducing the thickness x of the rotor blades 117, 118 and without risking delamination of hub 116 from drive shaft 4. In one aspect, the thickness y2 of hub 116 may be 50% of the thickness y1 of hub 16. As a result, the diameter z2 of hub 116 is less than the diameter z1 of hub 16. Moreover, in one aspect, the thickness y2 of hub 116 is approximately (e.g., +/−10%) equivalent to thickness x of rotor blades 117, 118. The reduced diameter z2 of hub 116 and the prevention of kinking in rotor blades 117, 118 while in the compressed state reduces the overall diameter of rotor 105 in the compressed state relative to rotor 5, which also reduces the diameter of pump housing 2 in the compressed state. Thus, when rotor 105 is used with pump 1, the reduced diameter of pump housing 2 in the compressed state may allow the arteriotomy incision into the patient through which the pump is implanted or inserted into the patient to be reduced. Furthermore, the rebound forces placed on the rotor 105 and inner coating of the pump housing 2 when rotor 105 is used may be reduced, which leads to reduced insertion and removal forces during deployment of the rotor 105 into the patient/removal of the rotor from the patient. For example, the design of rotor 105 is such that the outward radial force of the rotor blades when in the compressed state is reduced relative to the design of rotor 5. Thus, in the compressed state, rotor 105 may slide more easily through the component(s) of the delivery system (e.g., the introducer sheath) due to the reduced outward radial forces of rotor blades 117, 118 in the compressed state.

It is to be appreciated that, because the diameter z2 of rotor 105 is smaller than the diameter z1 of rotor 5, blades 117, 118 may extend a longer radial distance from hub 116 (compared to the distance that blades 17, 18 extend from hub 16), while still allowing rotors 5 and 105 to have the same expanded rotor diameter during use (while rotors 5, 105 are spinning). In this way, the larger radial length of rotor blades 117, 118, in relation to the length of rotor blades 17, 18 cause rotor 105 to be more efficient with respect to blood flow relative to rotor 5, despite having the same expanded rotor diameter during use.

It is to be appreciated that, during use of rotor 105 with pump 1, rotor 105 assumes further configurations in addition to the completely compressed configuration and the uncompressed or expanded configuration (when the rotor 105 is at rest). For example, when rotor 105 is rotated during use, due to centrifugal forces and the pressure of the fluid conveyed by rotor 105, the diameter of rotor 105 expands beyond the diameter of rotor 105 from its natural uncompressed and expanded configuration. Furthermore, the curvature of each of the blades 117, 118 is reduced or flattened when centrifugal and other pressure forces are placed thereon. These furthers configurations depend on the circumferential speed (i.e., rotation speed) of the rotor 105. The deformation to rotor 105 that occurs when additional stresses and strains may be placed upon the rotor during operation are small compared to the deformation of the rotor 105 from the compressed configuration to the natural expanded configuration (i.e., the configuration of the rotor with no stresses or strains placed thereon). In one aspect, rotor 105 is shaped and dimensioned such that any deformation of the rotor that occurs during use, when the rotor is subjected to the operational forces described herein, is controlled, minimized, or eliminated.

Avoiding the sharp kinking to blades 117, 118 in the compressed state reduces the maximum strain that is applied to the material of the rotor 105. Thus, the offset design of rotor 105 allows for the use of a broader choice of materials than what may be used with rotor 5. The broader choice of materials that may be used with rotor 105 may improve the manufacturability of rotor 105. For example, the extreme strain (e.g., up to 100% locally) on the material of rotor 5 during compression requires very stress resistant material(s) to be used, such as, polyurethane, which has a high level of crosslinking. In contrast, the reduced strain (e.g., up to 70% locally) on rotor 105 due to the offset design opens up the choices of useable materials from which to mold rotor 105. It is to be appreciated that local strains described herein refer to the stretch in the outer curvature of the bend in each of the rotor blades (i.e., the convex side of each of the blades) in relation to the neutral fiber (i.e., the mid line of each of the blades between the convex and concave sides) of the blades. For example, this outer curvature may be 180° in each of the rotor blades (e.g., the convex side) in some embodiments. Due to the bend (when the blades are folded) being configured differently in the design of rotor 105 (compared with rotor 5), the local stresses on rotor blades 117, 118 in rotor 105 are less as compared to the local stresses on rotor blades 17, 18 of rotor 5.

For example, the offset design allows the use of thermoplastic polyurethane, which has a relatively lower amount of crosslinking than the polyurethane used with rotor 5. The lower amount of crosslinking in the material used to mold rotor 105 allows an injection molding manufacturing process to be used to make rotor 105, which allows for more cost-effective mass production. This also may be the case for assure casting, vacuum molding, and/or lost-molds.

In one aspect, rotor 105 is molded onto drive shaft 4 as a single piece of elastomer with high flexibility and low hysteresis. For example, the rotor may be formed of a thermoplastic elastomer (TPE), such as a polyamide TPE (TPA), a copolyester TPE (TPC), a styrene TPE (TPS), a urethane TPE (TPU), a rubber crosslinked with TPE (TPV) or an acrylonitrile/butadiene rubber+polyvinyl chloride (TPZ). As another example, the rotor may be formed of polyolefin elastomer (TPO) or a thermoplastic polyamide elastomer. Other exemplary materials for manufacturing and molding rotor 105 in such a manner are described in U.S. Pat. No. 10,584,589, the entire contents of which are hereby incorporated by reference.

It is to be appreciated that the design of rotor 105 has an improved flow rate (higher flow in liters/min) relative to rotor 5 at the same maximum diameter of the rotors 5, 105 in the expanded state and with the same rotational speed. As described above, one explanation for the improved flow rate may be the comparatively larger radial length of rotor blades 117, 118, in relation to the length of rotor blades 17, 18 due to the reduction in the diameter of hub 116 relative to hub 16.

Moreover, the design of rotor 105 may mitigate hemolysis and other trauma to the blood as it flows past the rotor, as compared to rotor 5 at the same maximum diameter of the rotors 5, 105 and at the same rotational speed. In some aspects, use of rotor 105 mitigates hemolysis even at higher rotational speeds than the rotational speeds of rotor 5. With the same stress applied, the same amount of hemolysis may occur. With higher flow resulting from the design of rotor 105 relative to rotor 5, the trauma per volume may be reduced. In addition, with the higher flow velocities resulting from the design of rotor 105 relative to rotor 5, the length of time that the blood is subjected to the stress caused by the rotor may be reduced. Blood cells may tolerate short time stress much better than longer impact durations.

It is further to be appreciated that when rotor 105 is used with pump 1, an improved characteristic of flow (e.g., of the blood conveyed by pump 1) to motor current (e.g., the current of motor 6 during use of pump 1) and hydraulic pressure to motor current respectively may be realized. This improvement may enable the motor current signal of a pump controller that controls motor 6 together with the rotational speed of rotor 105 to be used to calculate in real time the flow of the blood conveyed by pump 1 without additional sensors. It is to be appreciated that such calculation may be performed by the pump controller 31 shown in FIG. 1 that controls motor 6 or another processor or controller of the pump system of the present technology. In this way, a desired flow may be maintained by a controller or processor (e.g., the pump controller 31) based on the calculation using the motor current signal and the rotation speed of rotor 105.

Figure 8:
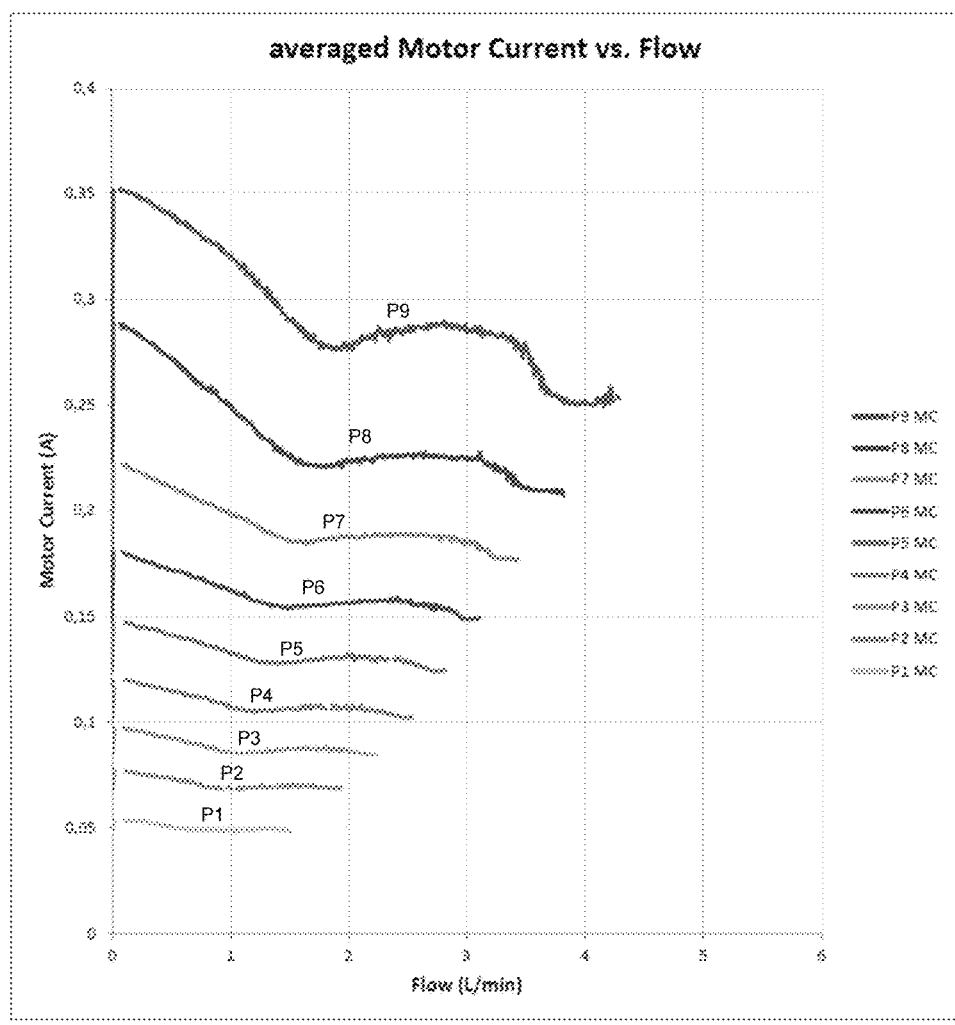
FIG. 8 is a chart illustrating characteristics of operation of the pump of FIG. 1 using the rotor of FIGS. 4A-4D in accordance with the present technology.

For example, referring to FIG. 8, a chart including curves plotting the motor current as compared to the flow of pump 1 using rotor 5 at different rotor speeds is shown in accordance with the present disclosure. The curves in FIG. 8 illustrate a plateau or counter slope. Since several of the curves in FIG. 8 have the same motor current, the flow for pump 1 while using rotor 5 cannot be calculated without further information.

Figure 9:
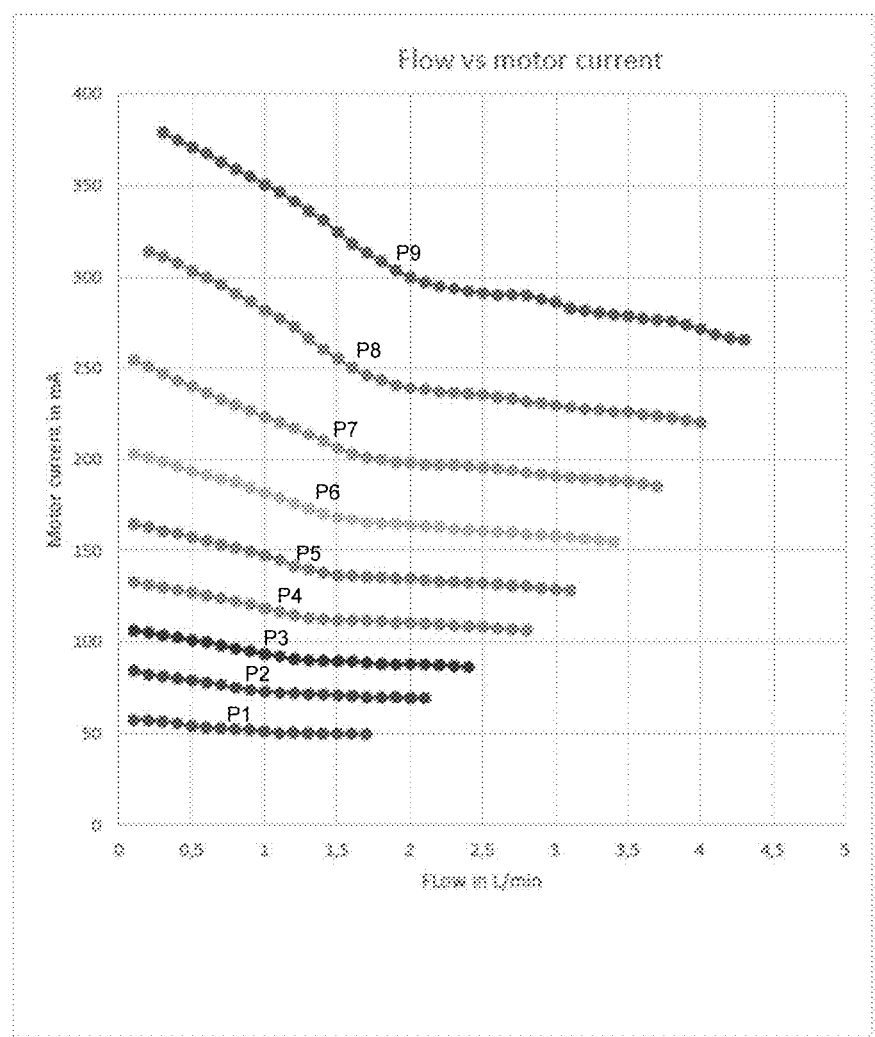
FIG. 9 is a chart illustrating characteristics of operation of the pump of FIG. 1 using the rotor of FIGS. 5A-5D in accordance with the present technology.

Referring to FIG. 9, a chart including curves plotting the motor current as compared to the flow of pump 1 using rotor 105 at different rotor speeds is shown in accordance with the present disclosure. The curves in FIG. 9 show that there is a strong monotonical relationship between the motor current and the flow when pump 1 is using rotor 105. Thus, when using rotor 105 with pump 1, the flow may be calculated (e.g., by a controller controlling motor 6 or another processor of the system) from the motor current of motor 6 without further information.

It is to be appreciated that the curves from bottom to top in FIGS. 8 and 9 correspond to the following rotor speeds used during testing: 15 krpm (kilo-revolutions per minute), 18 krpm, 20 krpm, 22 krpm, 24 krpm, 26 krpm, 28 krpm, 30 krpm, and 32 krpm. It is to be appreciated that 1000 rpm is equivalent to 1 krpm.

Comparing FIGS. 8 and 9, the above-described improvements in the operation of rotor 105 relative to rotor 5 may be noted with respect to the relationship between flow and motor current in FIGS. 8 and 9. In this regard, the relationship between the flow and motor current in FIG. 9 is more linear than the relationship illustrated in FIG. 8. Overall, differences in flow (at a given pressure) have less of a variable impact on motor current for rotor 105 compared with rotor 5. This indicates that the flow of the blood past rotor 105 is less turbulent than the flow of blood past rotor 5.

In one aspect, blades 117, 118 each include a monotonical taper over the length of each blade (draft angle) to improve unmolding the injection molded rotor 105. This draft angle may be directed axially and/or radially, depending on the mold-design.

Figure 5E:
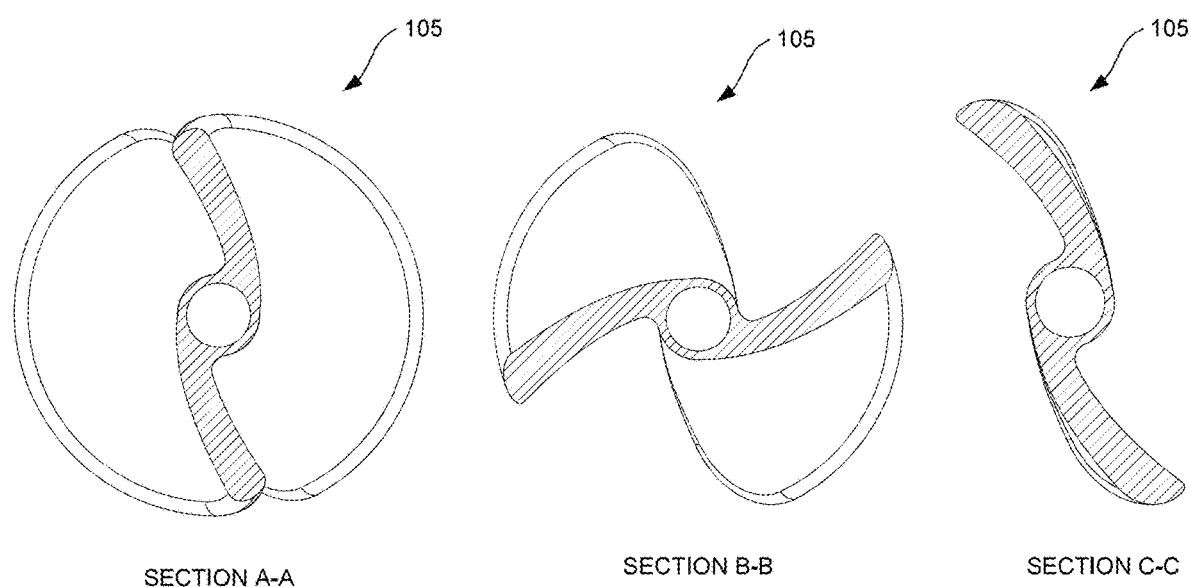
FIG. 5E includes cross-sectional views of the compressible and expandable rotor of FIGS. 5A-5D along sections A-A, B-B, and C-C shown in FIG. 5D in accordance with the present technology.

It is to be appreciated that as described above, in one aspect, portions 125, 126 of blades 117, 118 are offset with respect to axis 140 over the entire axial length of hub 116 (as shown in FIG. 5E). In other aspects, portions 125, 126 of blades 117, 118 may be offset with respect to axis 140 (orthogonal to rotational axis 130) only at selected points or portions axially along axis 130. For example, in one aspect, the distal portion of blade 117 at portion 125 and the distal portion of blade 118 at portion 126 may be offset a predetermined distance from axis 140, but the remainder of portions 125, 126 extends along radial axis 140 and do not include an offset. In another aspect, the proximal portion of blade 117 at portion 125 and the proximal portion of blade 118 at portion 126 may be offset a predetermined distance from axis 140, but the remainder of portions 125, 126 extends along radial axis 140 and may not include an offset. In another aspect, a central portion of each of portions 125, 126 between the distal and proximal ends 119, 120 of rotor 105 may be offset a predetermined distance from axis 140, but the distal and proximal portions of portions 125, 126 may not include an offset. In another aspect, portions 125, 126 may be offset over the entire axial length of hub 116, but the offset distance between portions 125, 126 of rotors 117, 118 and the radial axis may vary along the length of the hub 116. As described above, in one aspect, blades 117, 118 may include a constant helical pitch. A constant helical pitch may allow for easier unmolding of rotor 105 during manufacture. In other aspects, the pitch of rotor blades 117, 118 may be varied as desired. Moreover, rotor blades 117, 118 may include a quarter twist, a one-half twist, or as many multiple twists (or a fraction thereof) around the hub 116 as desired. Moreover, although two rotor blades 117, 118 are shown and described above with respect to rotor 105, rotor 105 may include a single rotor blade or any number of rotor blades without deviating from what is described herein. In this regard, the blades of rotor 105 may be varied in size, shape, and pitch, and may therefore be used for diverse applications.

In one aspect, the radial distance from hub 116 to the edges of each of blades 117, 118 may vary from one end of rotor 105 to another end of rotor 105 in a tapered manner. The degree of the taper may be constant or vary along the length of the hub. It is to be appreciated that the three-dimensional shape of rotor 105 may be modified with respect to what is shown in the figures and described herein to improve various aspects of the performance of a pump using rotor 105. Such aspects of the pump performance may include, but are not limited to, increased efficiency, increased pressure development, better flow to differential pressure relationship, or any other aspect of the pump performance that is affected based on the shape of rotor 105.

Although hub 116 is described above as being cylindrically shaped with a constant diameter along the length of hub 116, in other aspects, hub 116 may have a conical or frustoconical shape (i.e., a frustrum of a cone) such that hub 116 is tapered. Where hub 116 has a frustoconical shape, hub 116 includes a larger diameter at one end than the diameter at the opposite end. For example, referring to FIG. 10, hub 116 is shown with a diameter "b" at distal end 119 end that is smaller than a diameter "c" at proximal end 120 of hub 116. In one aspect, the taper in hub 116 may be monotonical over the length of hub 116. A tapered hub may enable easier unmolding of rotor 105.

Figure 10:
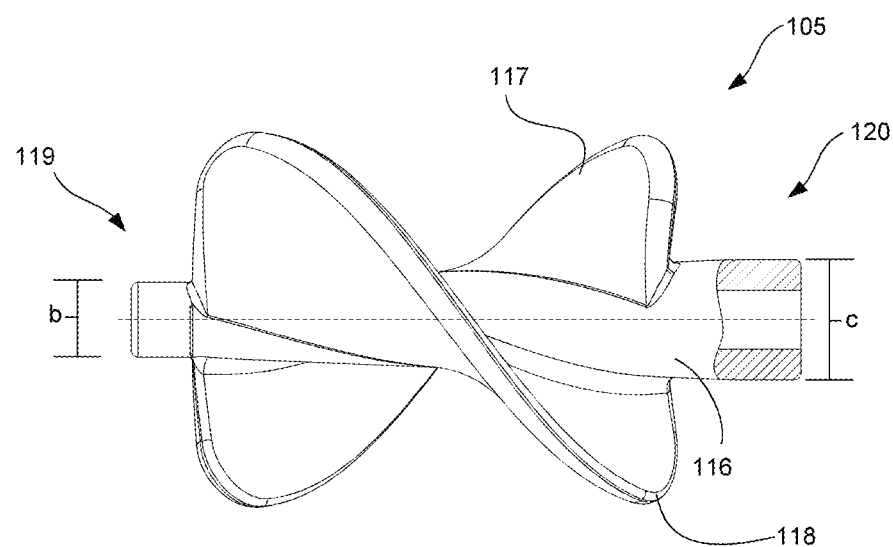
FIG. 10 is a side view of a compressible and expandable rotor in an uncompressed or expanded state and at rest including a tapered hub in accordance with the present technology.

It is to be appreciated that, as described above, the degree of offset between portions 125, 126 of blades 117, 118 with respect to axis 140 may vary at different axial positions along hub 116. The degree of offset axially along hub 116 may be affected by the taper/cylindricity of hub 116. For example, where rotor 105 includes a cylindrical hub 116 with a constant diameter over the length of hub 116, the degree of offset between each of portions 125, 126 of rotor blades 117, 118 and axis 140 may not vary along the length of hub 116. However, where rotor 105 includes a tapered hub 116, as shown in FIG. 10, the offset distance d of each of portions 125, 126 of blades 117, 118 with respect to axis 140 may vary from one end of hub 116 to the other end of hub 116. For example, the offset distance d will increase as the diameter of hub 116 decreases and the offset distance d will decrease as the diameter of hub 116 increases. In one aspect, at a central axial position of hub 116, the offset may resemble rotor configuration 60 described above with respect to FIG. 3B, toward end 119 of hub 116 where the diameter of hub 116 is relatively smaller the offset may resemble rotor configuration 80 described above with respect to FIG. 3D, and toward end 120 of hub 116 where the diameter of hub 116 is relatively larger the offset may resemble rotor configuration 70 described above with respect to FIG. 3C.

It is to be appreciated that, while rotor 105 is described above for use with a pump 1 including a flexible drive shaft 4 and an external motor 6 (located outside of the patient), rotor 105 may be used with any other type of fluid pump for conveying fluid. For example, rotor 105 may be arranged in a pump housing of a pump, such as a blood pump, that includes a rigid (non-flexible) drive shaft that rotor 105 is mounted to. This pump may include an onboard motor for driving the rigid drive shaft, where the motor is located in the pump housing or located proximately to the pump housing (e.g., at a proximal end of the pump housing).

From the foregoing and with reference to the various figure drawings, those skilled in the art will appreciate that certain modifications may also be made to the present disclosure without departing from the scope of the same. While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

The invention claimed is:

1. A pump comprising:
a pump housing that is expandable and compressible; and
a rotor that is expandable and compressible and disposed in the pump housing, the rotor comprising at least one rotor blade, a hub, and an axis of rotation,
wherein, in an uncompressed state of the rotor, at least a portion of the at least one rotor blade extends from the hub toward an outer edge of the at least one rotor blade along a first axis,
wherein the first axis is offset a predetermined distance from a radial axis of the rotor that orthogonally traverses the axis of rotation,
wherein the first axis is eccentric with respect to a center of the hub and substantial parallel to e radial axis.

2. The pump of claim 1, wherein the hub is cylindrically shaped.

3. The pump of claim 1, wherein a first end of the hub is tapered with respect to a second end of the hub.

4. The pump of claim 1, wherein the rotor is formed via injection molding, vacuum molding, assure casting, and/or lost-molds.

5. The pump of claim 1, wherein the rotor is formed from a single material.

6. The pump of claim 1, wherein the at least one rotor blade is a first rotor blade and the rotor further comprises a second rotor blade that extends from the hub toward an outer edge of the second rotor blade along a second axis that is offset the predetermined distance from the radial axis of the rotor, wherein the first axis and the second axis are offset to opposite sides of the radial axis and the second axis is eccentric with respect to a center of the hub and substantially parallel to the radial axis.

7. The pump of claim 1, wherein the at least one rotor blade is helically wound around the hub.

8. The pump of claim 7, wherein the at least one rotor blade includes a constant helical pitch.

9. The pump of claim 7, wherein the at least one rotor blade includes a varied pitch along a length of the hub.

10. The pump of claim 1, wherein the at least one rotor blade includes a concave side and a convex side.

11. The pump of claim 10, wherein, when the rotor is compressed to a compressed state, the concave side of the at least one rotor blade is laid against an exterior of the hub.

12. The pump of claim 10, wherein the first axis is offset from the radial axis in a direction of the convex side of the at least one rotor blade.

13. The pump of claim 12, wherein the first axis includes a spiral wound around the hub.

14. The pump of claim 13, wherein the spiral may include a constant pitch or a variable pitch.

15. The pump of claim 13, wherein the spiral includes a quarter twist, a one-half twist, or multiple twists around the hub.

16. The pump of claim 12, wherein, at the at least a portion of the at least one rotor blade, the convex side extends tangentially from the hub.

17. The pump of claim 1, further comprising a drive shaft including a proximal end and a distal end, wherein the hub of the rotor is mounted to the distal end of the drive shaft and the drive shaft is rotated to rotate the rotor.

18. The pump of claim 17, further comprising a motor coupled to the proximal end of the drive shaft, wherein the motor is configured to rotate the drive shaft.

19. The pump of claim 17, further comprising a catheter including a distal end coupled to a proximal end of the pump housing, wherein the drive shaft is disposed through a hollow interior of the catheter.

20. The pump of claim 1, wherein the pump is a blood pump and the pump housing includes an inlet and an outlet and rotation of the rotor conveys blood from the inlet to the outlet.

21. The pump of claim 17, wherein the pump housing is insertable into a heart of a patient.

22. The pump of claim 18, wherein the pump housing is insertable into a left ventricle of a heart of a patient.

23. The pump of claim 22, wherein an outlet of the pump is insertable into an aorta of the heart of the patient.

24. The pump of claim 1, wherein a convex side of the at least one rotor blade is a suction side of the at least one rotor blade and a concave side of the at least one rotor blade is a pressure side of the at least one rotor blade.

* * * * *

UNITED STATES PATENT AND TRADEMARK OFFICE
CERTIFICATE OF CORRECTION

PATENT NO. : 12,343,519 B2
APPLICATION NO. : 17/691635
DATED : July 1, 2025
INVENTOR(S) : Thorsten Siess et al.

It is certified that error appears in the above-identified patent and that said Letters Patent is hereby corrected as shown below:

In the Specification

Detailed Description
Column 5, Line 61:
Now reads: "housing 1"; should read -- housing 2 --

Detailed Description
Column 8, Line 17:
Now reads: "shaft 5."; should read -- shaft 4. --

Detailed Description
Column 13, Line 48:
Now reads: "rotors"; should read -- rotor blades --

In the Claims

Claim 1
Column 15, Line 18:
Now reads: "substantial"; should read -- substantially --

Claim 1
Column 15, Line 18:
Now reads: "e"; should read -- the --

Signed and Sealed this
Second Day of September, 2025

Coke Morgan Stewart
*Acting Director of the United States Patent and Trademark Office*